United States Patent
Zhu et al.

(10) Patent No.: US 9,248,246 B2
(45) Date of Patent: Feb. 2, 2016

(54) CATEGORY 1 M2M DEVICE DATA TRANSMISSION VIA A LONG TERM EVOLUTION NETWORK

(71) Applicant: Cellco Partnership, Basking Ridge, NJ (US)

(72) Inventors: Lily Zhu, Parsippany, NJ (US); Raafat Edward Kamel, Little Falls, NJ (US); Andrew E. Youtz, Princeton, NJ (US)

(73) Assignee: Cellco Partnership, Basking Ridge, NJ (US)

( * ) Notice: Subject to any disclaimer, the term of this patent is extended or adjusted under 35 U.S.C. 154(b) by 160 days.

(21) Appl. No.: 14/039,253

(22) Filed: Sep. 27, 2013

(65) Prior Publication Data

US 2015/0092590 A1    Apr. 2, 2015

(51) Int. Cl.
| | |
|---|---|
| *H04W 4/00* | (2009.01) |
| *A61M 11/00* | (2006.01) |
| *H04W 24/08* | (2009.01) |
| *H04L 1/00* | (2006.01) |
| *H04W 72/12* | (2009.01) |
| *A61M 15/00* | (2006.01) |

(52) U.S. Cl.
CPC ............ *A61M 11/008* (2014.02); *A61M 11/001* (2014.02); *A61M 11/005* (2013.01); *A61M 15/009* (2013.01); *A61M 15/0021* (2014.02); *A61M 15/0045* (2013.01); *H04L 1/00* (2013.01); *H04W 4/005* (2013.01); *H04W 24/08* (2013.01); *H04W 72/1242* (2013.01)

(58) Field of Classification Search
CPC . H04W 4/005; H04W 28/0215; H04W 72/02; H04W 72/04
USPC .................................................. 370/329–341
See application file for complete search history.

(56) References Cited

U.S. PATENT DOCUMENTS

| | | | |
|---|---|---|---|
| 2005/0030953 A1* | 2/2005 | Vasudevan et al. | 370/395.4 |
| 2012/0057476 A1* | 3/2012 | Chan et al. | 370/252 |
| 2012/0069803 A1* | 3/2012 | Iwamura et al. | 370/329 |
| 2013/0155987 A1* | 6/2013 | Lan et al. | 370/329 |
| 2014/0010187 A1* | 1/2014 | Huang et al. | 370/329 |
| 2014/0362831 A1* | 12/2014 | Young | 370/336 |

* cited by examiner

*Primary Examiner* — Kan Yuen

(57) ABSTRACT

A scheduler device may receive machine-to-machine (M2M) transmission information associated with a data transmission between a base station and a category 1 M2M device. The scheduler device may determine other transmission information associated with the base station. The other transmission information may include information associated with another data transmission between the base station and another device which is not a category 1 M2M device. The scheduler device may generate a resource assignment schedule associated with the category 1 M2M device and the other device. The resource assignment schedule may be based on the M2M transmission information and the other transmission information. The resource assignment schedule may identify a set of resources to be allocated to the category 1 M2M device during an increment of time. The scheduler device may provide the resource assignment schedule.

20 Claims, 9 Drawing Sheets

US 9,248,246 B2

CATEGORY 1 M2M DEVICE DATA TRANSMISSION VIA A LONG TERM EVOLUTION NETWORK

BACKGROUND

Machine-to-machine (M2M) communication refers to a technology that allows devices to communicate with one another over wired or wireless networks (e.g., a Long Term Evolution (LTE) network, a Universal Mobile Telecommunications System (UMTS) network, etc.) Generally, M2M communications may be characterized by periodic, semi-periodic, or on-demand transmission of small amounts of data. In some cases, M2M devices may be designed as relatively low cost devices that can be deployed by an end-user.

DETAILED DESCRIPTION

Figure 1A:
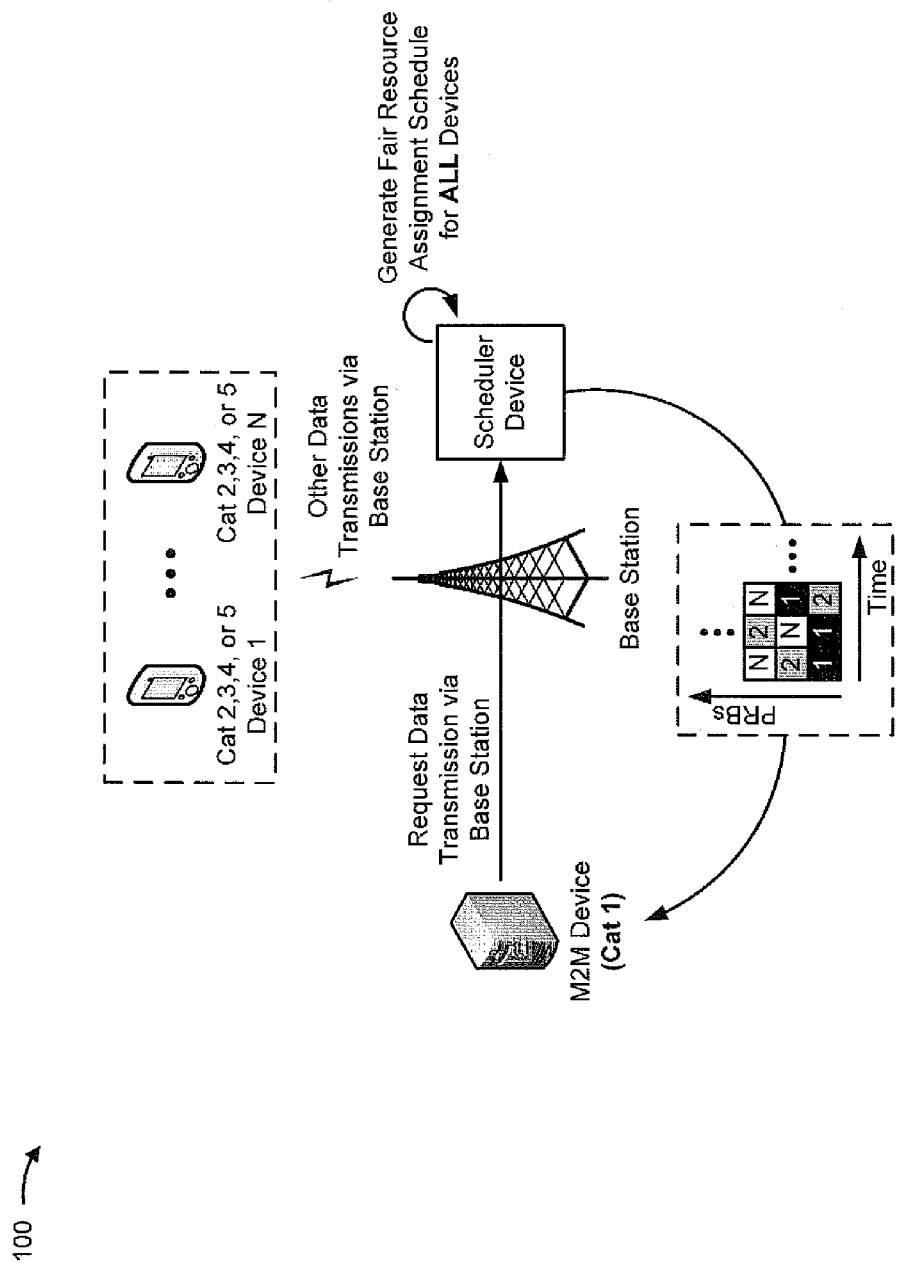
FIGS. 1A and 1B are diagrams of an overview of an example implementation described herein.

The following detailed description of example implementations refers to the accompanying drawings. The same reference numbers in different drawings may identify the same or similar elements.

A user may wish to connect an M2M device to a core network via an LTE radio access network that supports one or more categories of devices (e.g., category 1, category 2, category 3, etc.). However, the M2M device may not require a level of performance (e.g., a rate of data throughput, etc.) that the LTE network is capable of providing to the M2M device. For this reason, a cost associated with connecting the M2M device to the LTE network may be minimized by using a category of M2M device that supports a low peak data rate (e.g., a category 1 M2M device) to connect via the LTE network. In this way, the M2M device may enjoy the benefits of the LTE network (e.g., a low latency, a flat internet protocol ("IP") architecture, a unified core network, etc.). Moreover, allowing category 1 M2M devices to connect via the LTE network may reduce a quantity of M2M devices (e.g., other low cost M2M devices) that use older cellular networks (e.g., a second ("2G") generation network, a third generation ("3G") network, etc.) to connect to the core network.

A service provider associated with the core network may wish for all devices to connect to the core network using the LTE network (e.g., to allow all devices to enjoy benefits of the connecting via the LTE network). One way that the service provider may encourage all devices to connect via the LTE network is to allow the LTE network to support category 1 M2M devices that support a low peak data rate (e.g., a device that does not support multiple-input and multiple-output ("MIMO") technology) and/or that include a single receive antenna (e.g., where a dual receive antenna is required for a category 2 device, a category 3 device, a category 4 device, a category 5 device, a category 6 device, or a category 7 device).

The cost associated with a category 1 M2M device will be lower than a cost associated with a higher category M2M device (e.g., since category 1 devices support a lower data throughput than the higher category device, since MIMO support is not required for the category 1 device, etc.). However, the service provider may wish to ensure that a data transmission associated with a category 1 M2M device does not impact network service provided to other devices (e.g., since a category 1 M2M device may use a disproportionate amount of network resources when attempting to transfer a large amount of data). Implementations described herein may allow an LTE network to support a category 1 M2M device while allowing the service provider to monitor, schedule, and limit a data transmission associated with the category 1 M2M device (e.g., such that a network performance, associated with another device, is not impacted). In this way, network service, provided to other devices, may not be impacted by allowing the category 1 M2M device to communicate via an LTE network.

Figure 1B:
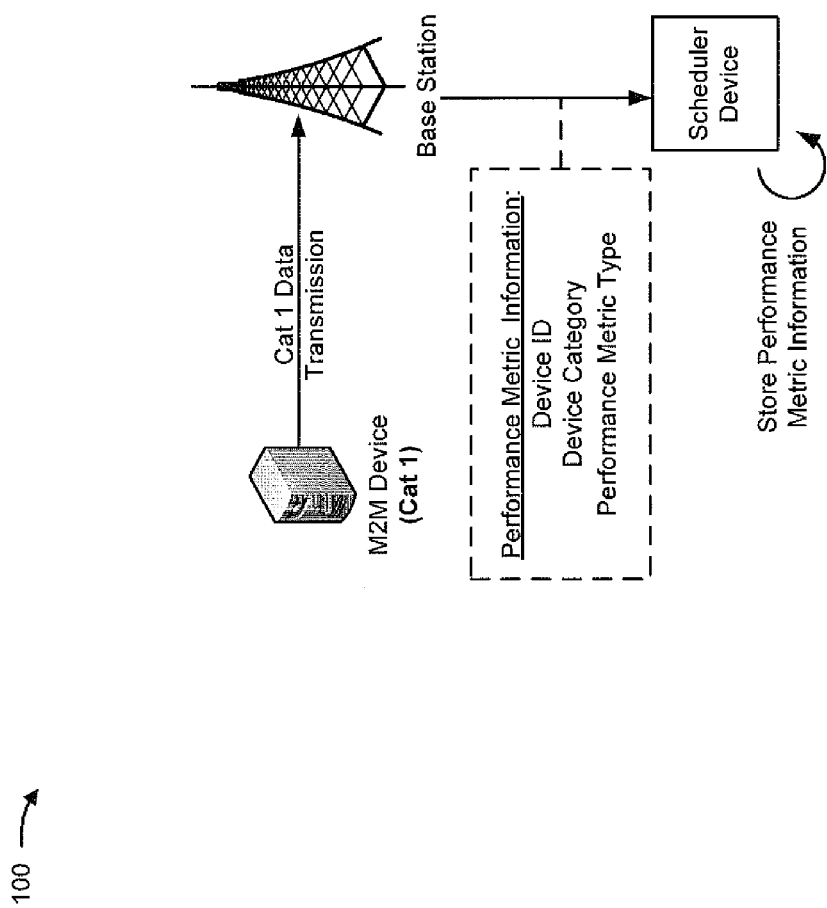

FIGS. 1A and 1B are diagrams of an overview of an example implementation 100 described herein. For the purposes of FIGS. 1A and 1B, assume that a category 1 M2M device wishes to establish a data transmission associated with a base station included in an LTE network. Further, assume that a group of N devices (e.g., including devices of higher categories) are already communicating (e.g., transmitting data) with the base station.

As shown in FIG. 1A, the category 1 M2M device may send, to the base station, a request to establish the data transmission (e.g., alternatively, the base station may initiate the data transfer by requesting to send data to the category 1 M2M device (not shown)). As shown, the base station may forward the request to a scheduler device associated with the base station. The base station may also send information associated with each data transmission associated with each of the N devices communicating with the base station. As further shown, the scheduler device may receive the information associated with the request and the information associated with the other data transmissions, and may generate a resource assignment schedule. The resource assignment schedule may also be based on information identifying the M2M device as a category 1 device (e.g., the scheduler device may determine that the category 1 M2M device is not to transmit at a data rate exceeding a maximum data rate).

As shown, the resource assignment schedule may include information that identifies one or more physical resource blocks ("PRBs") assigned to each device for an increment of time (e.g., a millisecond ("ms")). Since a category 1 device cannot support a peak data rate as high as a higher category device, a modulation and coding scheme ("MCS") value selection, associated with the category 1 device, may be limited to a low MCS value. Therefore, the "fairness" of a schedule may not focus on fair data throughput, but rather on the over-the-air physical resources (e.g., PRBs). As further shown, the scheduler device provide the schedule to the category 1 M2M device (e.g., via the base station). As shown, the scheduler device may generate the resource assignment schedule for additional increments of time, and may provide the schedule (e.g., PRBs assigned to each device for each increment of time) to the category 1 M2M device. In this manner, the scheduler device may ensure that each device is allocated a fair amount of resources (e.g., an equal quantity of PRBs over period of time) such that network performance is not impacted by allowing the category 1 M2M device to send and/or receive data via the LTE network.

For the purposes of FIG. 1B, assume that a category 1 M2M device is transmitting data to a base station included in an LTE network in accordance with a resource assignment schedule generated by a scheduler device. Further, assume that the base station detects a performance metric (e.g., a throughput, a failure event, etc.), and that base station is to send information identifying the performance metric to the scheduler device for storage. As shown in FIG. 1B, the base station may send information (e.g., a device identifier and/or category identifier associated with the category 1 M2M device, a performance metric type, etc.) to the scheduler device. As further shown in FIG. 1B, the scheduler device may store the transmission information associated with the performance metric (e.g., to allow the service provider to track performance metrics associated only with category 1 M2M devices).

In this way, a service provider may schedule, manage, and/or monitor a data transmission associated with a category 1 M2M device such that the category 1 M2M device may communicate with a base station included an LTE network, without affecting network service to other devices communicating with the base station.

Figure 2:
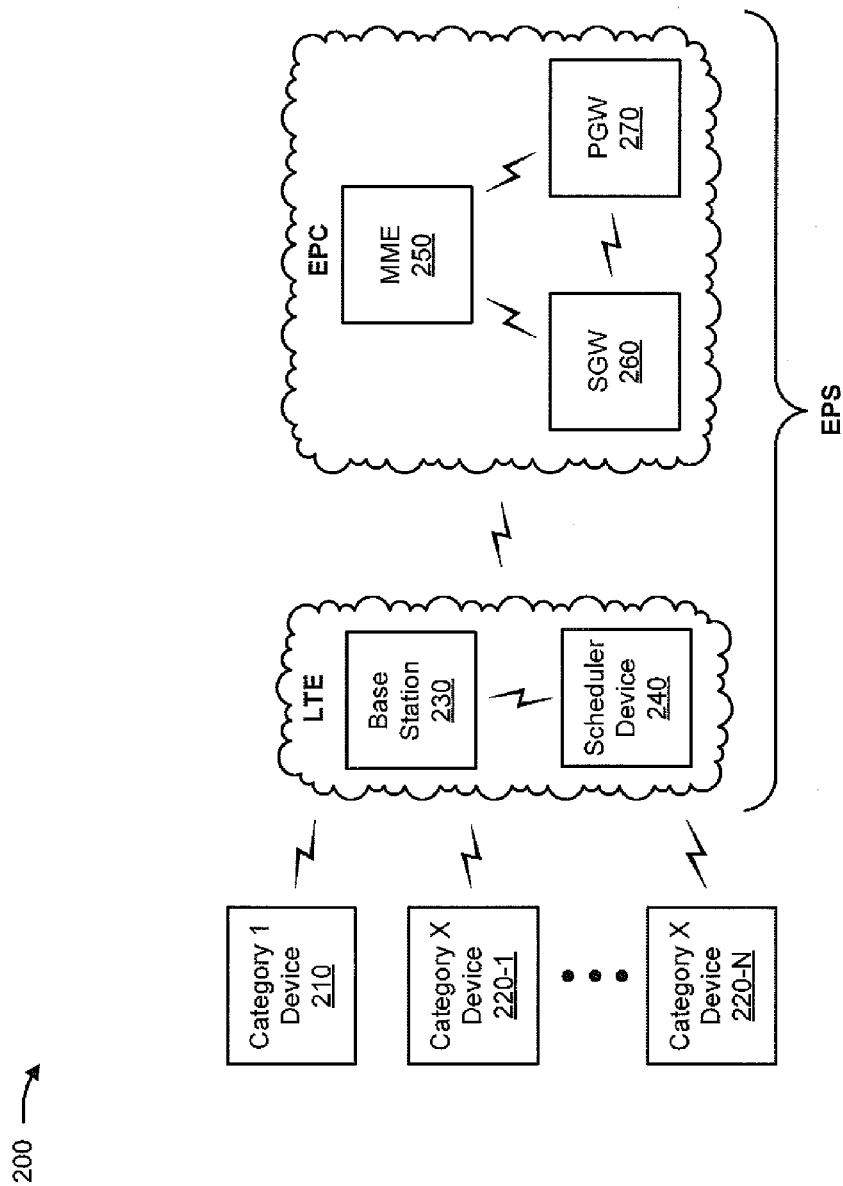
FIG. 2 is a diagram of an example environment in which systems and/or methods, described herein, may be implemented.

FIG. 2 is a diagram of an example environment 200 in which systems and/or methods described herein may be implemented. As shown in FIG. 2, environment 200 may include category 1 device 210, a set of category X devices 220-1 through 220-N(N≥1) (hereinafter collectively referred to as "category X devices 220," and individually as "category X device 220"), a base station 230, a scheduler device 240, a mobility management entity device 250 (hereinafter referred to as "MME 250"), a serving gateway 260 (hereinafter referred to as "SGW 260"), and a packet data network gateway 270 (hereinafter referred to as "PGW 270").

Implementations described herein may be performed within a long term evolution ("LTE") network. Environment 200 may include an evolved packet system ("EPS") that includes the LTE network and/or an evolved packet core ("EPC") that operate based on a third generation partnership project ("3GPP") wireless communication standard. The LTE network may be a radio access network ("RAN") that includes base station 230 that takes the form of an evolved Node B ("eNodeB") via which category 1 device 210 and/or category X devices 220 may communicate with the EPC. The EPC may include MME 250, SGW 260, and PGW 270 that enable category 1 device 210 and/or category X devices 220 to communicate with another network and/or device associated with the EPS.

Category 1 device 210 may include a category 1 M2M device that may be capable of communicating with the EPC via base station 230. For example, category 1 device 210 may include a network device (e.g., a modem, a switch, a gateway, etc.), a sensing device, a processing device, a metering device, and/or some other type of device. In some implementations, category 1 device 210 may include a sensing or metering device to gather data and form a data record associated with the data. In some implementations, category 1 device 210 may include another type of device that gathers, stores, processes, and/or transmits data (e.g., a category 1 mobile device, etc.).

In some implementations, category 1 device 210 may include a single receive antenna that may be used to communicate with base station 230. In some implementations, category 1 device 210 may include a device with a lower peak rate (e.g., a lower uplink data rate, a lower downlink data rate, etc.) than a higher category device (e.g., a category 2 device, a category 3 device, etc.). In some implementations, category 1 device 210 may include a device that does not support MIMO. In some implementations, category 1 device 210 may receive, from scheduler device 240, a data transmission schedule before sending and/or receiving data to and/or from base station 230.

Category X device 220 may include may include a category 2 device, a category 3 device, a category 4 device, or a category 5 device that may be capable of communicating with the EPC via base station 230. For example, user device 210 may include a wired communication device, a wireless communication device, a radiotelephone, a personal communications system ("PCS") terminal (e.g., that may combine a cellular radiotelephone with data processing and data communications capabilities), a personal digital assistant ("PDA") (e.g., that can include a radiotelephone, a pager, Internet/intranet access, etc.), a smart phone, a desktop computer, a laptop computer, a tablet computer, and/or a similar device. In some implementations, category X device 220 may include a device with a higher peak rate (e.g., a higher uplink data rate, a higher downlink data rate, etc.) than a lower category device (e.g., a category 2 device may have a higher peak rate than a category 1 device, etc.). In some implementations, category X device 220 may receive, from scheduler device 240, a data transmission schedule before sending and/or receiving data to and/or from base station 230.

Base station 230 may include a device capable of transferring traffic, such as audio, video, text, and/or other traffic, destined for and/or received from category 1 device 210 and/or category X device 220. In some implementations, base station 230 may include an eNodeB associated with the LTE network that receives traffic from and/or sends traffic via SGW 260 and/or PGW 270. Base station 230 may send traffic to and/or receive traffic from category 1 device 210 and/or category X device 220 via an air interface. In some implementations, base station 230 may be associated with a small cell, such as a microcell, a picocell, and/or a femtocell. In some implementations, base station 230 may send and/or receive information, associated with a data transmission, to and/or from scheduler device 240. Additionally, or alternatively, base station 230 may include scheduler device 240.

Scheduler device 240 may include a device, such as a server, capable of receiving, generating, processing, storing, and/or providing information associated with a data transmission between category 1 device 210 and base station 230 and/or a data transmission between category X device 220 and base station 230. For example, scheduler device 240 may receive data transmission information, from base station 230 (e.g., information associated with a data transmission schedule, information associated with a performance metric, information associated with a failure event, etc.) and may manage the data transmission based on the transmission information. In some implementations, scheduler device 240 may be capable of generating and providing a resource assignment schedule, associated with one or more data transmission, for one or more increments of time. In some implementations, scheduler device 240 may manage, process, and/or monitor a data transmission associated with category 1 device 210 and/or category X device 220. While being shown as being located external to base station 230, scheduler device 240 may be implemented within base station 230.

MME 250 may include a device capable of managing authentication, activation, deactivation, and mobility functions associated with category 1 device 210 and/or category X device 220. For example, MME 250 may include a server. In some implementations, MME 250 may perform operations relating to authentication of category 1 device 210 and/or category X device 220. Additionally, or alternatively, MME 250 may facilitate the selection of a SGW 260 and/or PGW 270 to serve traffic to and/or from category 1 device 210 and/or category X device 220. Additionally, or alternatively, MME 250 may perform an operation associated with handing off category 1 device 210 and/or category X device 220 from a first base station 230 to a second base station 230.

SGW 260 may include a device capable of routing user data packets. For example, SGW 260 may include one or more data processing and/or traffic transfer devices, such as a gateway, a router, a modem, a switch, a firewall, a network interface card ("NIC"), a hub, a bridge, a server, an optical add/drop multiplexer ("OADM"), or any other type of device that processes and/or transfers traffic. SGW 260 may also receive traffic from a network and/or other network devices, and may send the received traffic to category 1 device 210 and/or category X device 220 via base station 230. Additionally, or alternatively, SGW 260 may perform operations associated with handing off category 1 device 210 and/or category X device 220 to and/or from the LTE network.

PGW 270 may include a device capable of providing connectivity for category 1 device 210 and/or category X device 220 to external packet data networks (e.g., other than the depicted EPC and/or LTE network). For example, PGW 270 may include one or more data processing and/or traffic transfer devices, such as a gateway, a router, a modem, a switch, a firewall, a NIC, a hub, a bridge, a server, an OADM, or any other type of device that processes and/or transfers traffic. In some implementations, PGW 270 may receive traffic from another network and may send the traffic to category 1 device 210 and/or category X device 220 via SGW 260.

The number of devices and networks shown in FIG. 2 is provided for explanatory purposes. In practice, there may be additional devices and/or networks, fewer devices and/or networks, different devices and/or networks, or differently arranged devices and/or networks than those shown in FIG. 2. Furthermore, two or more of the devices shown in FIG. 2 may be implemented within a single device, or a single device shown in FIG. 2 may be implemented as multiple, distributed devices. Additionally, one or more of the devices of environment 200 may perform one or more functions described as being performed by another one or more of the devices of environment 200. Devices of environment 200 may interconnect via wired connections, wireless connections, or a combination of wired and wireless connections.

Figure 3:
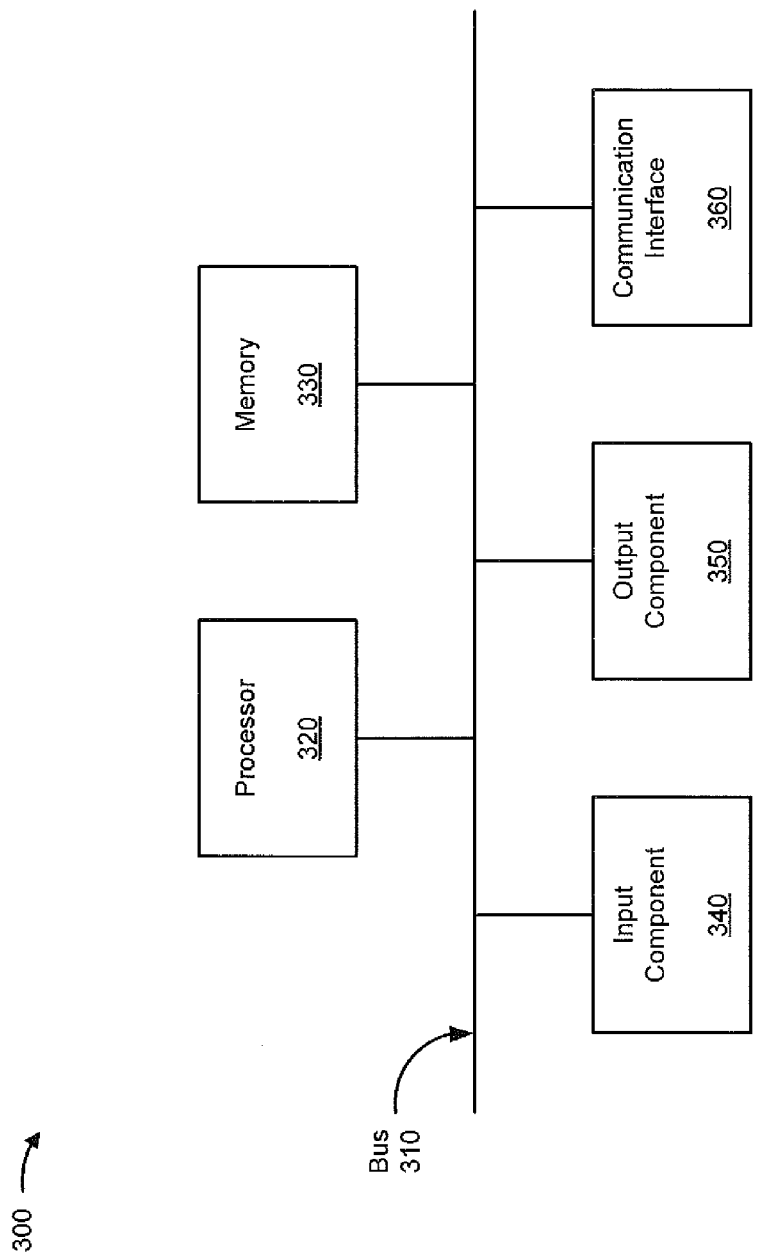
FIG. 3 is a diagram of example components of one or more devices of FIG. 2.

FIG. 3 is a diagram of example components of a device 300. Device 300 may correspond to category 1 device 210, category X device 220, base station 230, scheduler device 240, MME 250, SGW 260, and/or PGW 270. Additionally, or alternatively, each of category 1 device 210, category X device 220, base station 230, scheduler device 240, MME 250, SGW 260, and/or PGW 270 may include one or more devices 300 and/or one or more components of device 300. As shown in FIG. 3, device 300 may include a bus 310, a processor 320, a memory 330, an input component 340, an output component 350, and a communication interface 360.

Bus 310 may include a path that permits communication among the components of device 300. Processor 320 may include a processor, a microprocessor, and/or any processing component (e.g., a field-programmable gate array ("FPGA"), an application-specific integrated circuit ("ASIC"), etc.) that interprets and/or executes instructions. In some implementations, processor 320 may include one or more processor cores. Memory 330 may include a random access memory ("RAM"), a read only memory ("ROM"), and/or any type of dynamic or static storage device (e.g., a flash memory, a magnetic memory, an optical memory, etc.) that stores information and/or instructions for use by processor 320.

Input component 340 may include any component that permits a user to input information to device 300 (e.g., a keyboard, a keypad, a mouse, a button, a switch, etc.). Output component 350 may include any component that outputs information from device 300 (e.g., a display, a speaker, one or more light-emitting diodes ("LEDs"), etc.).

Communication interface 360 may include any transceiver-like component, such as a transceiver and/or a separate receiver and transmitter, that enables device 300 to communicate with other devices and/or systems, such as via a wired connection, a wireless connection, or a combination of wired and wireless connections. For example, communication interface 360 may include a component for communicating with another device and/or system via a network. Additionally, or alternatively, communication interface 360 may include a logical component with input and output ports, input and output systems, and/or other input and output components that facilitate the transmission of data to and/or from another device, such as an Ethernet interface, an optical interface, a coaxial interface, an infrared interface, a radio frequency ("RF") interface, a universal serial bus ("USB") interface, or the like.

Device 300 may perform various operations described herein. Device 300 may perform these operations in response to processor 320 executing software instructions included in a computer-readable medium, such as memory 330. A computer-readable medium may be defined as a non-transitory memory device. A memory device may include memory space within a single physical storage device or memory space spread across multiple physical storage devices.

Software instructions may be read into memory 330 from another computer-readable medium or from another device via communication interface 360. When executed, software instructions stored in memory 330 may cause processor 320 to perform one or more processes that are described herein. Additionally, or alternatively, hardwired circuitry may be used in place of or in combination with software instructions to perform one or more processes described herein. Thus, implementations described herein are not limited to any specific combination of hardware circuitry and software.

The number of components shown in FIG. 3 is provided for explanatory purposes. In practice, device 300 may include additional components, fewer components, different components, or differently arranged components than those shown in FIG. 3.

Figure 4:
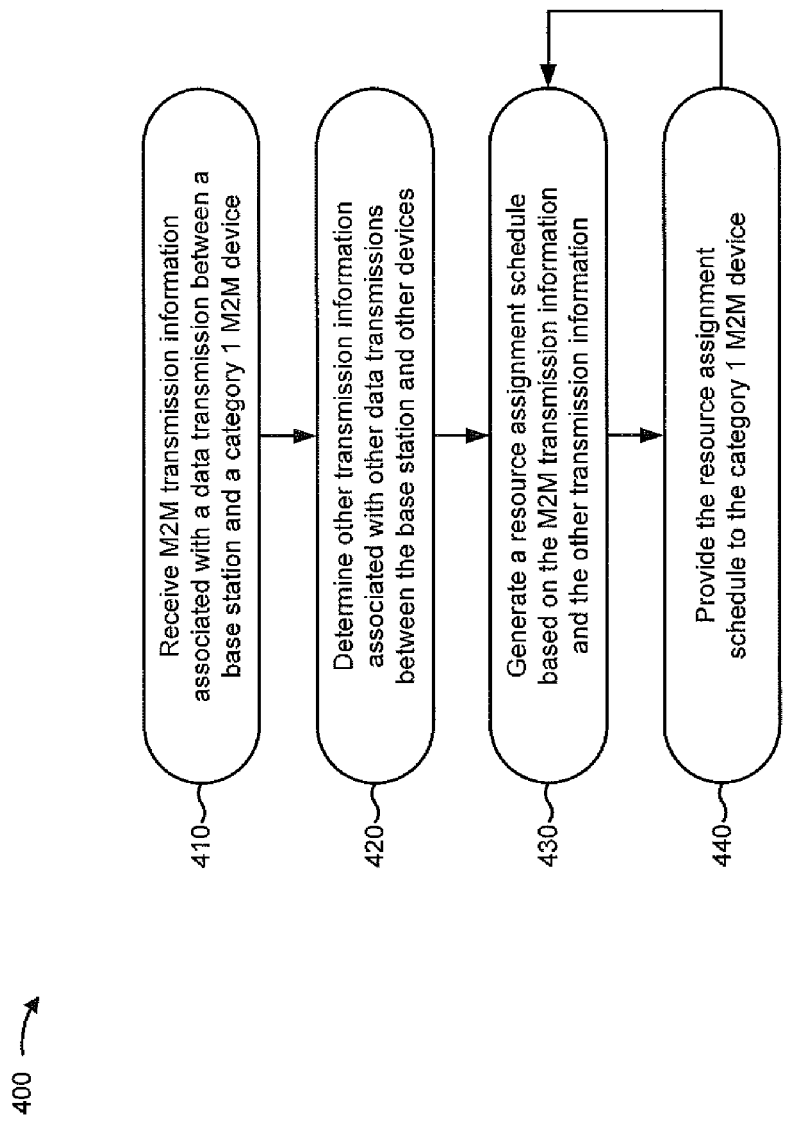
FIG. 4 is a flow chart of an example process for generating a resource assignment schedule associated with a category 1 M2M device using an LTE network.

FIG. 4 is a flow chart of an example process 400 for generating a resource assignment schedule associated with a category 1 M2M device using an LTE network. In some implementations, one or more process blocks of FIG. 4 may be performed by scheduler device 240. In some implementations, one or more process blocks of FIG. 4 may be performed by another device or a group of devices separate from or including scheduler device 240, such as base station 230.

As shown in FIG. 4, process 400 may include receiving M2M transmission information associated with a data transmission between a base station and a category 1 M2M device (block 410). For example, scheduler device 240 may receive M2M transmission information, associated with a data transmission between a base station 230 and a category 1 device 210, from base station 230. Additionally, or alternatively, scheduler device 240 may receive the M2M transmission information from category 1 device 210.

In some implementations, scheduler device 240 may receive the M2M transmission information when base station 230 receives the M2M transmission information from category 1 device 210 (e.g., when category 1 device 210 sends a request, associated with the data transmission, to base station 230). Additionally, or alternatively, scheduler device 240 may receive the M2M transmission information from base station 230 when base station 230 determines that base station 230 is to transmit data, to category 1 device 210, based on information received from another device (e.g., SGW 260, PGW 270, etc.).

M2M transmission information may include information associated with a transmission of data between category 1 device 210 and a base station 230. For example, the transmission information may include information associated with establishing the data transmission, such as an amount of data to be transmitted, information indicating that category 1 device 210 is a category 1 device, information associated with assigning a resource block (e.g., a channel quality indicator ("CQI"), etc.) or the like. In some implementations, the M2M transmission information may be used, by base station 230 and/or scheduler device 240, to determine a resource assignment schedule, a modulation and coding scheme ("MCS") associated with the data transmission, the amount of data (e.g., included in a quantity of resource blocks) to be transmitted in an increment of time associated with the resource assignment schedule, or the like.

As further shown in FIG. 4, process 400 may include determining other transmission information associated with other data transmissions between the base station and other devices (block 420). For example, scheduler device 240 may determine transmission information associated with other data transmissions between base station 230 and category X devices 220. As an additional example, base station 230 may determine the other transmission information, may send the other transmission information to scheduler device 240, and scheduler device 240 may determine the other transmission information based on receiving the transmission information. In some implementations, scheduler device 240 may determine the other transmission information based on information stored by scheduler device 240 (e.g., where scheduler device 240 stores information associated with the other transmissions).

In some implementations, scheduler device 240 may determine the other transmission information when scheduler device 240 receives the M2M transmission information from base station 230. Additionally, or alternatively, scheduler device 240 may determine the other transmission information when scheduler device 240 determines (e.g., based on information received from base station 230) that a resource assignment schedule, associated with base station 230, is to be generated.

Other transmission information may include information associated with other data transmissions (e.g., other than the data transmission between category 1 device 210 and base station 230) between category X devices 220 and base station 230. For example, the other transmission information may include information associated with the other data transmission, such as an amount of data to be transmitted, information indicating the category of category X device 220 (e.g., category 1, category, category 3, category 5, etc.), or other information associated with scheduling the other data transmission (e.g., an MCS index number, etc.). In some implementations, scheduler device 240 may determine other transmission information associated with multiple data transmissions between multiple category X devices 220 and base station 230. In some implementations, the other transmission information may include transmission information associated with another category 1 M2M device (e.g., where category X device 220 may be a category 1 M2M device).

As further shown in FIG. 4, process 400 may include generating a resource assignment schedule based on the M2M transmission information and the other transmission information (block 430). For example, scheduler device 240 may generate a resource assignment schedule, associated with category 1 device 210 and category X devices 220, based on the M2M transmission information and the other transmission information. In some implementations, scheduler device 240 may generate the resource assignment schedule when scheduler device 240 determines the other transmission information and/or when scheduler device 240 receives the M2M transmission information.

In some implementations, scheduler device 240 may generate the resource assignment schedule when scheduler device 240 determines information associated with a performance metric associated with the data transmission between category 1 device 210 and base station 230. For example, scheduler device 240 may determine that a data rate, associated with the data transmission between category 1 device 210 and base station 230, exceeds a maximum allowable data rate, and may generate a resource assignment schedule based on determining the date rate.

A resource assignment schedule may include information identifying one or more PRBs that are to be allocated (e.g., to a data transmission between category 1 device 210 and base station 230, to a data transmission between category X device 220 and base station 230, etc.) during an increment of time. A PRB may include a minimum amount of data that can be transmitted by base station 230. For example, each PRB may be include twelve frequency (e.g., 15 megahertz ("MHz")) subcarriers across one 0.5 ms time slot. Each frequency subcarrier may include multiple resource elements, and each resource element may include one LTE symbol. Each LTE symbol may carry multiple bits associated with a data transmission (e.g., where the quantity of bits carried by each resource element depends on a MCS index number selected by scheduler device 240 and/or base station 230).

In some implementations, the resource assignment schedule may include information identifying one or more PRBs that are to be allocated to the data transmission in a time slot (e.g., 0.5 ms), a subframe (e.g., 1 ms), a frame (e.g., 10 ms), or another increment. In some implementations, scheduler device 240 may generate the resource assignment schedule based on a total quantity of devices (e.g., a quantity of category 1 devices 210, a quantity of category X devices 220) associated with base station 230. Additionally, or alternatively, scheduler device 240 may generate a resource assignment schedule that includes information identifying multiple PRBs such that each device is assigned an equal quantity of PRBs during a period of time (e.g., 1 ms, 10 ms, 1 second, 2 minutes etc.). For example, category 1 device 210 may be assigned three PRBs during a first increment of time (e.g., 1 ms), and category X device 220 may be assigned two PRBs during the first increment of time. Assuming scheduler device 240 is to assign PRBs equally over two increments of time, scheduler device 240 may assign two PRBs to category 1 device 210 during a second increment of time (e.g., 1 ms), and may assign three PRBs to category X device 220 during the second increment of time (e.g., category 1 device 210 and category X device 220 would each be assigned five PRBs over the two increment period of time). In some implementations, the period of time may be configurable by a service provider associated with scheduler device 240.

Additionally, or alternatively, scheduler device 240 may generate a resource assignment schedule based on information associated with each category 1 device 210 and information associated with each category X device 220. For example, scheduler device 240 may generate a resource assignment schedule that includes information identifying multiple PRBs that are to be assigned to each of the total quantity of devices based on a priority associated with each of the total quantity of devices (e.g., where a category X device 220, that is a category 2, 3, 4 or 5 device may have a higher priority that category 1 device 210, and may be assigned PRBs before category 1 device 210 may be assigned PRBs). As an additional example, scheduler device 240 may generate a resource assignment schedule based on one or more factors associated with each category 1 device 210 and/or each category X device 220, such as an RF condition associated with each device, a data back log associated with each device, a category associated with each device, or the like.

In some implementations, scheduler device 240 may generate the resource assignment schedule to limit the data rate of category 1 device 210. For example, scheduler device 240 may determine information indicating that category 1 device 210 is transmitting data at a particular data rate that exceeds a maximum allowable data rate (e.g., a data rate specified by the service provider) for a transmission associated with category 1 device 210, and scheduler device 240 may generate a resource assignment schedule that may limit the data rate (e.g., by assigning fewer PRBs to the data transmission associated with category 1 device 210 for a period of time). Additionally, or alternatively, scheduler device 240 may limit the data transmission by providing, to category 1 device 210 and/or base station 230, information indicating that the data transmission is to be limited. In this way, scheduler device 240 may prevent a data transmission, between category 1 device 210 and base station 230, from using a quantity of resources in such a way that the data transmission may affect another data transmission (e.g., a data transmission between category X device 220 and base station 230).

In some implementations, scheduler device 240 may generate the resource assignment schedule when scheduler device 240 receives information identifying a failure event associated with category 1 device 210 and/or category X device 220. For example, scheduler device 240 may receive information identifying a failure event associated with a data transmission between category X device 220 and base station 230, and may generate an updated resource assignment schedule (e.g., an updated resource assignment schedule based on the data transmission being interrupted).

As further shown in FIG. 4, process 400 may include providing the resource assignment schedule to the category 1 M2M device (block 440). For example, scheduler device 240 may provide the resource assignment schedule to category 1 device 210. In some implementations, scheduler device 240 may provide the resource assignment schedule to base station 230, and base station 230 may send the resource assignment schedule to category 1 device 210.

In some implementations, scheduler device 240 may provide the resource assignment schedule to category 1 device 210 when scheduler device 240 generates the resource assignment schedule. Additionally, or alternatively, scheduler device 240 may provide the resource assignment schedule to category 1 device 210 when scheduler device 240 receives (e.g., from base station 230) information indicating that a base station 230 is to send and/or receive data from category 1 device 210 and/or category X device 220.

In this way, category 1 device 210 and/or category X device 220 may receive a resource assignment schedule that identifies PRBs to be used for a data transmission, and category 1 device 210 and/or category X device 220 may identify when to send and/or receive data based on the resource assignment schedule.

In some implementations, scheduler device 240 may generate an additional resource assignment schedule (e.g., for a next period of time) after scheduler device 240 has provided the resource assignment schedule. For example, scheduler device 240 may generate a resource assignment schedule, identifying PRBs to be assigned to one or more data transmissions, for a one hundred millisecond period of time. Scheduler device 240 may then generate and provide an additional resource assignment schedule (e.g., for the next one hundred millisecond increment of time) in the manner discussed above.

Although FIG. 4 shows example blocks of process 400, in some implementations, process 400 may include additional blocks, different blocks, fewer blocks, or differently arranged blocks than those depicted in FIG. 4. Additionally, or alternatively, two or more of the blocks of process 400 may be performed in parallel.

Figure 5A:
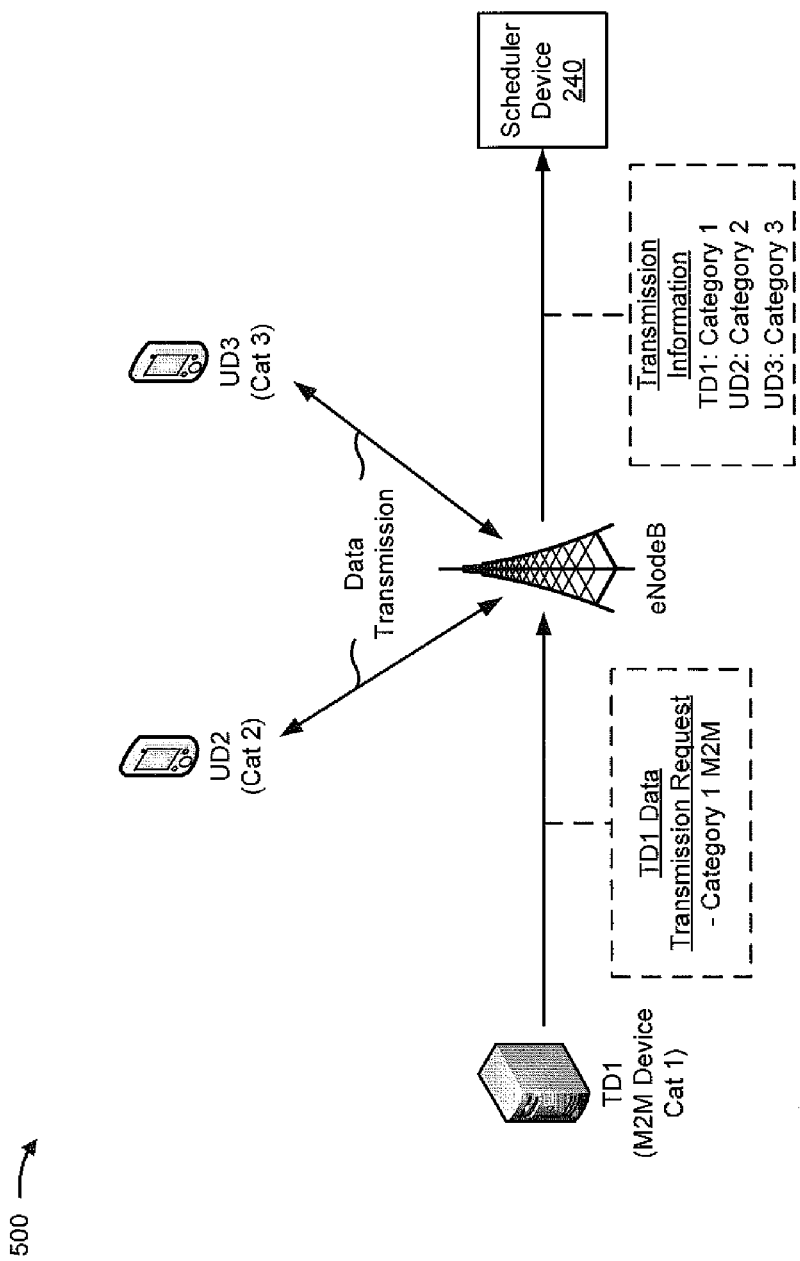
FIGS. 5A and 5B are diagrams of an example implementation relating to the example process shown in FIG. 4.
Figure 5B:
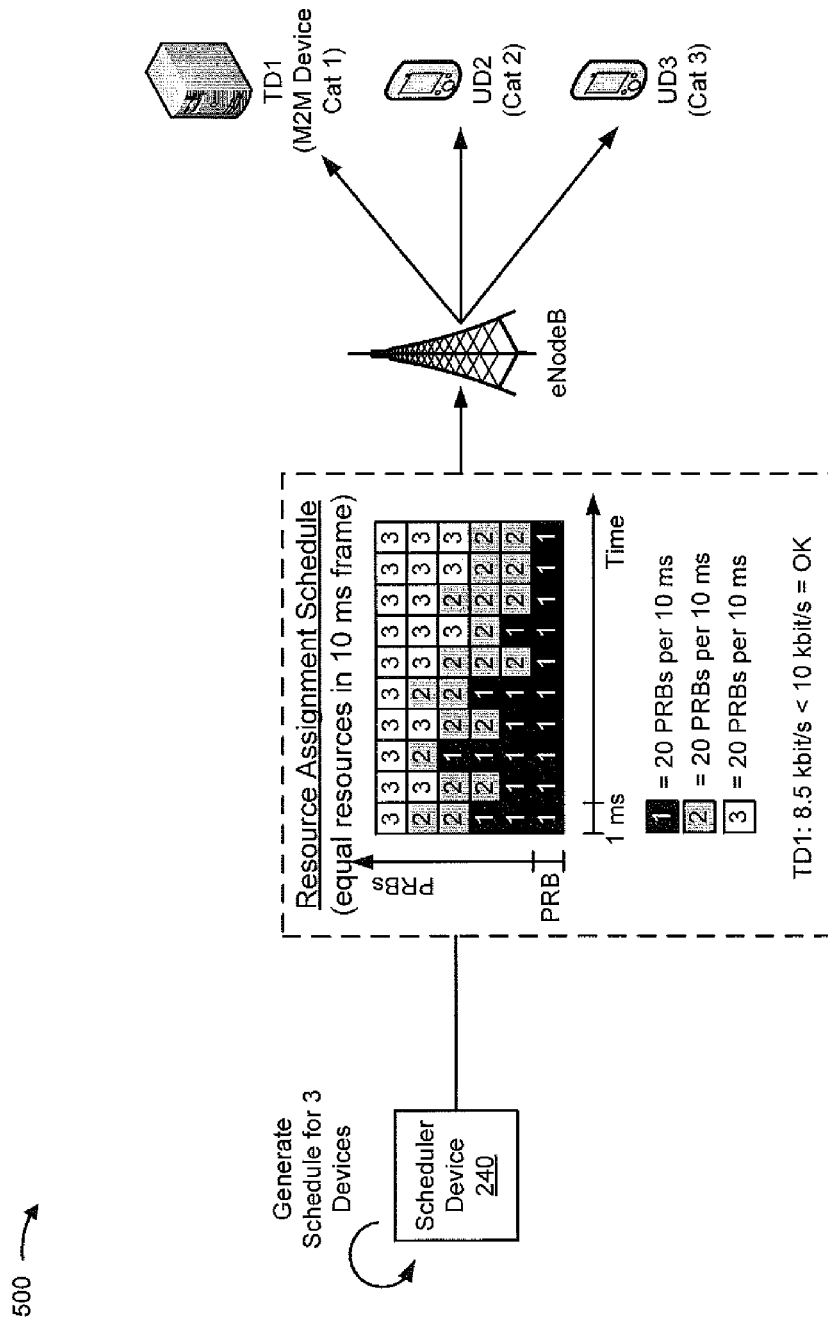

FIGS. 5A and 5B are diagrams of an example implementation 500 relating to example process 400 shown in FIG. 4. For the purposes of example implementation 500, assume that a category 1 M2M device, identified as TD1, wishes to receive data from an LTE base station, identified as eNodeB, included in an LTE network. Further, assume that there are two other devices connected to the LTE network via eNodeB, identified as UD2 and UD3. Finally, assume that UD2 and UD3 are category 2 and category 3 devices, respectively.

As shown in FIG. 5A, TD1 may send a request to eNodeB to establish a data transmission. As shown, the request may contain M2M transmission information indicating that TD1 is a category 1 M2M device. As further shown, eNodeB may determine that eNodeB is supporting a data transmission between category 2 UD2 and eNodeB, and is supporting a data transmission between category 3 UD3 and eNodeB.

As further shown, eNodeB may provide transmission information, associated with TD1, UD2, and UD3, to scheduler device 240. As shown, the transmission information received by scheduler device 240 may contain information indicating a category associated with each device (e.g., category 1 for TD1, category 2 for UD2, category 3 for UD3).

For the purposes of FIG. 5B, assume that scheduler device 240 is configured to generate a resource assignment schedule for increments of 1 ms, and that there are six PRBs that may be assigned to a device during each 1 ms increment. Further, assume that, when scheduling for a category 1 M2M device, scheduler device 240 is generate a resource assignment schedule such that each device is to be assigned an equal number of PRBs over a period of 10 ms (e.g., to ensure that a particular device does not use a disproportionate amount of network resources).

As shown in FIG. 5B, scheduler device 240 may determine that scheduler device 240 is configured to generate the resource assignment schedule (e.g., based on receiving the transmission information from eNodeB), and may generate a resource assignment schedule for a first millisecond of data transmission. As shown, the resource assignment schedule for the first millisecond may indicate that, during the first millisecond, TD1 is to use a set of three PRBs, UD2 is to be assigned a set of two PRBs, and UD3 is to be assigned one PRB (e.g., the quantity of PRBs assigned to each device does not need to be equal). As further shown, scheduler device 240 may then generate a resource assignment schedule for a second millisecond of data transmission. As shown, the resource assignment schedule for the second millisecond may indicate that, during the second millisecond, TD1 is to use a set of two PRBs, UD2 is to be assigned a set of two PRBs, and UD3 is to be assigned a set of two PRBs.

As further shown in FIG. 5B, scheduler device 240 may continue generating resource assignment schedules for a period of 10 ms. As shown, the schedule may include information indicating that TD1, UD2, and UD3 are to be assigned an equal number (e.g., 20) of PRBs over the 10 ms period of time (e.g., where there are 60 total PRBs available in the 10 ms timeframe).

As shown, scheduler device 240 may monitor (e.g., as the resource assignment schedule for the 10 one millisecond increments is generated) a data rate, based on the quantity of PRBs assigned to TD1 over a period of time (e.g., the previous one second), to ensure that the data rate at which TD1 transmits data does not exceed a maximum data rate of 10 kilobits per second. As shown, scheduler device 240 may determine that the data rate associated with TD1 is 8.5 kilobits per second (e.g., scheduler device has assigned 8.5 kilobits of PRBs during the previous one second), and scheduler device 240 need not limit the quantity of PRBs assigned to TD1 to lower the data rate. In this way, scheduler device 240 may monitor the data rate and prevent TD1 from using a disproportionate amount of network resources (e.g., network performance for UD2 and UD3 will not be affected due to TD1 attempting to transmit data at a rate that exceeds the maximum allowable rate). As further shown, scheduler device 240 may provide the resource assignment schedule to eNodeB, and eNodeB may send the schedule to TD1, UD2, and UD3.

As indicated above, FIGS. 5A and 5B are provided merely as an example. Other examples are possible and may differ from what was described with regard to FIGS. 5A and 5B.

Figure 6:
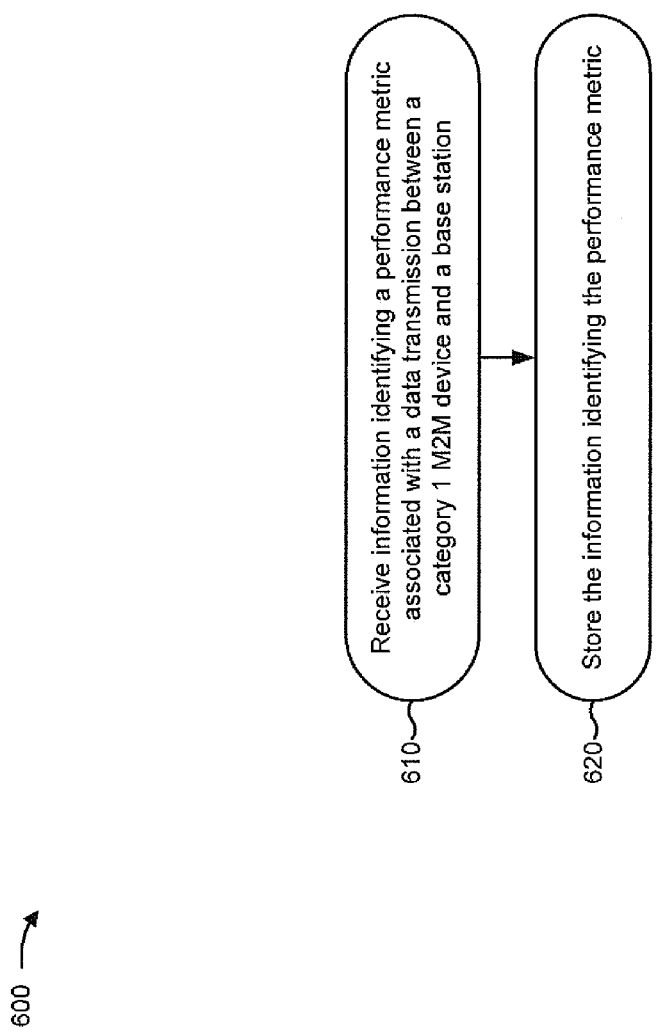
FIG. 6 is a flow chart of an example process for receiving and storing information identifying a performance metric associated with a category 1 M2M device.

FIG. 6 is a flow chart of an example process 600 for receiving and storing information identifying a performance metric associated with a category 1 M2M device. In some implementations, one or more process blocks of FIG. 6 may be performed by scheduler device 240. In some implementations, one or more process blocks of FIG. 6 may be performed by another device or a group of devices separate from or including scheduler device 240, such as base station 230.

As shown in FIG. 6, process 600 may include receiving information identifying a performance metric associated with a data transmission between a category 1 M2M device and a base station (block 610). For example, scheduler device 240 may receive information identifying a performance metric associated with a data transmission between category 1 device 210 and base station 230. In some implementations, scheduler device 240 may receive the information from base station 230 when base station 230 detects the performance metric. In some implementations, scheduler device 240 may receive the information identifying the performance metric from another device associated with the data transmission (e.g., MME 250, SGW 260, PGW 270, etc.).

A performance metric may be a measurement associated with the data transmission between category 1 device 210 and base station 230. For example, the performance metric may include a rate of processing, (e.g., a bandwidth rate, a throughput, etc.), an error rate (e.g., an amount of latency, an amount of jitter, a packet dropping probability, a bit error rate, etc.), a measurement of time associated with processing (e.g., a maximum turn-around time, a maximum mean time to recover, etc.), a failure event (e.g., a radio link failure, a handover failure, etc.), or the like. In some implementations, the information identifying the performance metric may include the type of performance metric (e.g., a failure event, a throughput, etc.), information that identifies category 1 device 210 (e.g., information indicating that category 1 device 210 is a category 1 device), information that identifies base station 230, and/or other information associated with the data transmission. In some implementations, as discussed above, scheduler device 240 may generate a resource assignment schedule based on receiving the information identifying the performance metric.

As further shown in FIG. 6, process 600 may include storing the information identifying the performance metric (block 620). For example, scheduler device 240 may store the information identifying the performance metric associated with the data transmission between category 1 device 210 and base station 230.

In some implementations, scheduler device 240 may store information associated with the performance metric, such as a device identifier (e.g., a string of characters, a serial number, etc.) that identifies a category 1 device 210 associated with the performance metric, a base station identifier that identifies base station 230, or the like. In some implementations, scheduler device 240 may store the information identifying the performance metric in a memory location (e.g., a RAM, a hard disk, etc.) of scheduler device 240, and scheduler device 240 may store an indication that the performance metric is associated with category 1 device 210 and/or base station 230. Additionally, or alternatively, scheduler device 240 may transmit the information identifying the performance metric to another device (e.g., a device associated with base station 230, etc.) for storage.

In some implementations, scheduler device 240 may store the information identifying the performance metric to allow a service provider, associated with the LTE network, to track performance metrics associated with category 1 M2M devices (e.g., where the service provider wishes for performance metrics associated with higher category devices to be tracked separately). For example, the service provider may wish to track average data throughput, associated with each category of device (e.g., since the data throughput for category 1 devices 210 may be lower than the data throughput for higher category X devices 220), such that a performance metric, associated with data throughput of higher category X devices 220, is not impacted by the lower data throughput associated with category 1 devices 210. In some implementations, scheduler device 240 may store the information identifying the performance metric, and may send the information to another device (e.g., a device associated with aggregating category 1 performance metrics).

Although FIG. 6 shows example blocks of process 600, in some implementations, process 600 may include additional blocks, different blocks, fewer blocks, or differently arranged blocks than those depicted in FIG. 6. Additionally, or alternatively, two or more of the blocks of process 600 may be performed in parallel.

Figure 7:
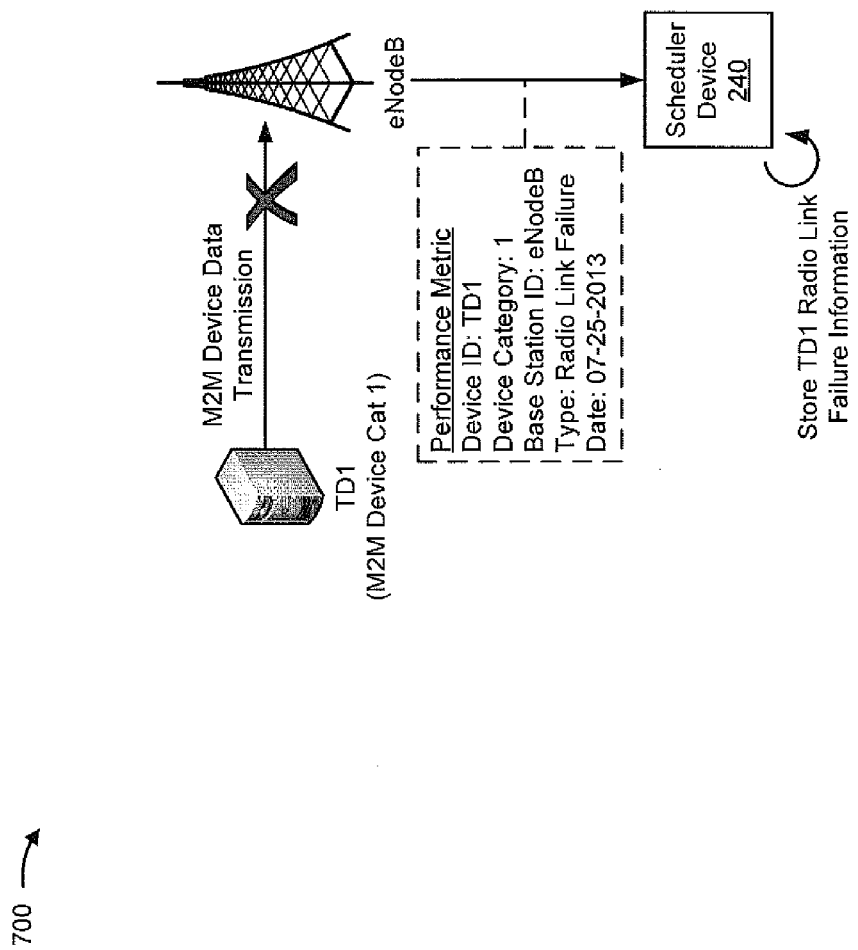
FIG. 7 is a diagram of an example implementation relating to the example process shown in FIG. 6.

FIG. 7 is a diagram of an example implementation 700 relating to example process 600 shown in FIG. 6. For the purposes of example implementation 700, assume that a category 1 M2M device is in the process of transmitting a quantity of data to a base station included in an LTE network (e.g., an eNodeB).

As shown in FIG. 7, the air interface between the category 1 M2M device and the eNodeB may degrade (e.g., due to the use of a single receive antenna), and the radio link, between the category 1 M2M device and the eNodeB, may fail. As shown, the eNodeB may detect the radio link failure event, and may provide, to scheduler device 240, information identifying the performance metric (e.g., the failure event). As shown, the information identifying the performance metric may include a device identifier associated with the category 1 M2M device (e.g., TD1), information identifying TD1 as a category 1 device, information identifying the base station (e.g., eNodeB), information indicating the type of performance metric (e.g., radio link failure), and information indicating a date associated with the performance metric (e.g., Jul. 25, 2013). As further shown in FIG. 7, scheduler device 240 may store the information identifying the performance metric in a memory location associated with scheduler device 240.

As indicated above, FIG. 7 is provided merely as an example. Other examples are possible and may differ from what was described with regard to FIG. 7.

Implementations described herein may allow an LTE network to support a category 1 M2M device, and may allow the service provider to monitor, schedule, and/or limit a data transmission associated with the category 1 M2M device. In this way, network service to other devices may not be impacted, and the service provider may monitor and/or manage usage of network resources by a category 1 M2M device.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

Some implementations are described herein in conjunction with thresholds. The term "greater than" (or similar terms), as used herein to describe a relationship of a value to a threshold, may be used interchangeably with the term "greater than or equal to" (or similar terms). Similarly, the term "less than" (or similar terms), as used herein to describe a relationship of a value to a threshold, may be used interchangeably with the term "less than or equal to" (or similar terms). As used herein, "satisfying" a threshold (or similar terms) may be used interchangeably with "being greater than a threshold," "being greater than or equal to a threshold," "being less than a threshold," "being less than or equal to a threshold," or other similar terms.

To the extent the aforementioned implementations collect, store, or employ personal information provided by individuals, it should be understood that such information shall be used in accordance with all applicable laws concerning protection of personal information. Storage and use of personal information may be in an appropriately secure manner reflective of the type of information, for example, through various encryption and anonymization techniques for particularly sensitive information.

It will be apparent that systems and/or methods, as described herein, may be implemented in many different forms of software, firmware, and hardware in the implementations shown in the figures. The actual software code or specialized control hardware used to implement these systems and/or methods is not limiting of the implementations. Thus, the operation and behavior of the systems and/or methods were described without reference to the specific software code—it being understood that software and control hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Where only one item is intended, the term "one" or similar language is used. Further, the phrase "based on" is intended to mean "based, at least in part, on" unless explicitly stated otherwise.

What is claimed is:

1. A scheduler device, comprising:
a memory; and
one or more processors to:
receive machine-to-machine (M2M) transmission information associated with a first data transmission between a base station and an M2M device;
determine information identifying a data rate associated with the first data transmission between the base station and the M2M device;
identify a maximum allowable data rate associated with the first data transmission between the base station and the M2M device;
determine that the data rate exceeds the maximum allowable data rate;
determine other transmission information associated with the base station,
the other transmission information including information associated with a second data transmission between the base station and another device which is not a M2M device;
generate, based on determining that the data rate exceeds the maximum allowable data rate, a resource assignment schedule associated with the M2M device and the other device,
the resource assignment schedule being based on the M2M transmission information and the other transmission information, and
the resource assignment schedule identifying a set of resources to be allocated to the M2M device during an increment of time; and
provide the resource assignment schedule.

2. The scheduler device of claim 1,
where the one or more processors are further to:
select a modulation and coding scheme for the M2M device based on the M2M transmission information; and
where the one or more processors, when generating the resource assignment schedule, are to:
generate the resource assignment schedule based on the modulation and coding scheme for the M2M device.

3. The scheduler device of claim 1, where the one or more processors, when generating the resource assignment schedule, are to:
identify a first set of physical resource blocks to be allocated to the data transmission between the base station and the M2M device for a particular increment of time; and
identify a second set of physical resource blocks to be allocated to the data transmission between the base station and the other device for the particular increment of time.

4. The scheduler device of claim 1,
where the one or more processors are further to:
determine that the M2M device and the other device are to be allocated an equal quantity of resources over a period of time,
the period of time comprising multiple increments of time; and where the one or more processors, when generating the resource assignment schedule, are to:
    generate the resource assignment schedule based on determining that the M2M device and the other device are to be allocated an equal quantity of resources over the period of time.

5. The scheduler device of claim 1, where the one or more processors, when providing the resource assignment schedule, are to:
    provide the resource assignment schedule to the M2M device and the other device.

6. The scheduler device of claim 1, where the one or more processors are further to:
    receive information identifying a performance metric associated with the M2M device identified in the resource assignment schedule; and
    store the information identifying the performance metric.

7. The scheduler device of claim 1, the M2M device requiring a level of performance that is less than a level of performance that a Long Term Evolution (LTE) network is capable of providing.

8. A non-transitory computer-readable medium storing instructions, the instructions comprising:
    one or more instructions that, when executed by one or more processors, cause the one or more processors to:
        receive first transmission information associated with a data transmission between a M2M device and a base station;
        determine information identifying a data rate associated with the data transmission between the base station and the M2M device;
        identify a maximum allowable data rate associated with the first data transmission between the base station and the M2M device;
        determine that the data rate exceeds the maximum allowable data rate;
        obtain second transmission information associated with the base station,
            the second transmission information including information associated with another data transmission between the base station and another device that is not a M2M device;
        generate, based on determining that the data rate exceeds the maximum allowable data rate, a resource assignment schedule, associated with the M2M device and the other device,
            the resource assignment schedule being based on the first transmission information and the second transmission information, and
            the resource assignment schedule including information associated with resources that are to be allocated to the M2M device; and
        transmit the resource assignment schedule.

9. The non-transitory computer-readable medium of claim 8,
    where the one or more instructions, when executed by the one or more processors, cause the one or more processors to:
        select a modulation and coding scheme for the M2M device based on the first transmission information; and
    where the one or more instructions, that cause the one or more processors to generate the resource assignment schedule, cause the one or more processors to:
        generate the resource assignment schedule based on the modulation and coding scheme for the M2M device.

10. The non-transitory computer-readable medium of claim 8, where the one or more instructions, that cause the one or more processors to generate the resource assignment schedule, cause the one or more processors to:
    identify a first set of physical resource blocks to be allocated to the data transmission between the base station and the M2M device for a particular increment of time; and
    identify a second set of physical resource blocks to be allocated to the data transmission between the base station and the other device for the particular increment of time.

11. The non-transitory computer-readable medium of claim 8,
    where the one or more instructions, when executed by the one or more processors, further cause the one or more processors to:
        determine that the M2M device and the other device are to be allocated a particular quantity of resources over a period of time,
            the period of time comprising multiple increments of time; and
    where the one or more instructions, that cause the one or more processors to generate the resource assignment schedule, further cause the one or more processors to:
        generate the resource assignment schedule based on determining that the M2M device and the other device are to be allocated the particular quantity of resources over the period of time.

12. The non-transitory computer-readable medium of claim 8, where the one or more instructions further cause the one or more processors to:
    receive information identifying a performance metric associated with the M2M device identified in the resource assignment schedule; and
    store the information identifying the performance metric.

13. The non-transitory computer-readable medium of claim 8, where the one or more instructions, that cause the one or more processors to transmit the resource assignment schedule, cause the one or more processors to:
    transmit the resource assignment schedule to the base station.

14. The non-transitory computer-readable medium of claim 8, the M2M device requiring a level of performance that is less than a level of performance that a Long Term Evolution (LTE) network is capable of providing.

15. A method, comprising:
    receiving, by a device, transmission information,
        the transmission information being associated with a data transmission between a base station and a first device;
    determining, by the device, information identifying a data rate associated with the data transmission between the base station and the first device;
    identifying, by the device, a maximum allowable data rate associated with the data transmission between the base station and the first device;
    determining, by the device, that the data rate exceeds the maximum allowable data rate;
    identifying, by the device, other transmission information associated with the base station,
        the other transmission information being associated with another data transmission between the base station and a second device;

generating, by the device and based on determining that the data rate exceeds the maximum allowable data rate, a resource assignment schedule associated with the device and the second device,
- the resource assignment schedule being based on the transmission information and the other transmission information, and
- the resource assignment schedule identifying network resources to be allocated to the first device; and sending, by the device, the resource assignment schedule to the first device.

16. The method of claim 15, further comprising:

selecting a modulation and coding scheme for the first device based on the transmission information,
- where generating the resource assignment schedule comprises:
  - generating the resource assignment schedule based on the modulation and coding scheme for the first device.

17. The method of claim 15, where generating the resource assignment schedule comprises:

identifying a first set of physical resource blocks to be allocated to the data transmission between the base station and the first device for a particular increment of time; and identifying a second set of physical resource blocks to be allocated to the data transmission between the base station and another device for the particular increment of time.

18. The method of claim 15, further comprising:

determining that the first device and the second device are to be allocated an equal quantity of resources over a period of time,
- the period of time comprising multiple increments of time,
  - where generating the resource assignment schedule further comprises:
    - generating the resource assignment schedule based on determining that the first device and the second device are to be allocated an equal quantity of resources over the period of time.

19. The method of claim 15, further comprising:

receiving information identifying a performance metric associated with the first device identified in the resource assignment schedule; and store the information identifying the performance metric.

20. The method of claim 15, where the first device requires a level of performance that is less than a level of performance that a Long Term Evolution (LTE) network is capable of providing.

* * * * *